United States Patent
Heinrich et al.

(10) Patent No.: US 8,287,497 B2
(45) Date of Patent: Oct. 16, 2012

(54) ACCESS ASSEMBLY WITH FLEXIBLE HOUSING

(75) Inventors: Russell Heinrich, Madison, CT (US); Michael Bettuchi, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 171 days.

(21) Appl. No.: 12/774,169

(22) Filed: May 5, 2010

(65) Prior Publication Data
US 2010/0324489 A1 Dec. 23, 2010

Related U.S. Application Data

(60) Provisional application No. 61/219,017, filed on Jun. 22, 2009.

(51) Int. Cl.
*A61M 5/178* (2006.01)
(52) U.S. Cl. ................................. 604/167.01
(58) Field of Classification Search ............... 604/164.1, 604/164.11, 164.01–164.08; 600/208; 606/108, 606/213
See application file for complete search history.

(56) References Cited

U.S. PATENT DOCUMENTS

| | | |
|---|---|---|
| 4,601,710 A | 7/1986 | Moll |
| 5,030,206 A | 7/1991 | Lander |
| 5,127,909 A | 7/1992 | Shichman |
| 5,290,304 A | 3/1994 | Storace |
| 5,354,280 A | 10/1994 | Haber et al. |
| 5,391,153 A | 2/1995 | Haber et al. |
| 5,407,433 A | 4/1995 | Loomas |
| 5,492,304 A | 2/1996 | Smith et al. |
| 5,522,831 A | 6/1996 | Sleister et al. |
| 5,549,565 A | 8/1996 | Ryan et al. |
| 5,634,908 A | 6/1997 | Loomas |
| 5,657,963 A | 8/1997 | Hinchliffe et al. |
| 7,632,250 B2 | 12/2009 | Smith et al. |
| 2004/0068232 A1* | 4/2004 | Hart et al. ............ 604/167.06 |
| 2006/0047284 A1 | 3/2006 | Gresham |
| 2007/0004968 A1* | 1/2007 | Bonadio et al. ............ 600/208 |
| 2008/0091144 A1 | 4/2008 | Moran et al. |
| 2009/0005738 A1* | 1/2009 | Franer ............ 604/164.01 |

FOREIGN PATENT DOCUMENTS

EP 1219251 7/2002

* cited by examiner

*Primary Examiner* — Christopher D Koharski

(57) ABSTRACT

An access assembly includes a housing defining a longitudinal axis and having a longitudinal opening therethrough, a cannula extending distally from the housing and in fluid communication with the longitudinal opening and a seal member mounted within the longitudinal opening of the housing. The seal member is configured to receive an instrument therethrough in substantial sealed relation therewith. The housing is adapted to move in at least a radial direction with respect to the longitudinal axis whereby the seal member maintains the substantial sealed relation relative to the instrument as the instrument in manipulated. The housing may be flexible and capable of deflection relative to the longitudinal axis. The housing may comprise an elastomeric material in whole or in part. The seal member may be integrally formed with the housing. The housing may include at least one flexible ring portion and possibly a plurality of ring portions.

9 Claims, 5 Drawing Sheets

ACCESS ASSEMBLY WITH FLEXIBLE HOUSING

CROSS REFERENCE TO RELATED APPLICATION

The present application claims the benefit of and priority to U.S. Provisional Application Ser. No. 61/219,017 filed on Jun. 22, 2009, the entire contents of which are incorporated herein by reference.

BACKGROUND

1. Technical Field

The present disclosure relates to trocars and other access assemblies. More particularly, the present disclosure relates to an access assembly having a flexible housing.

2. Background of Related Art

Trocars and other access assemblies are used by surgeons to operate on a patient without having to create large incisions that may become infected and may cause major scaring. Trocar assemblies are known in the art, as are the instruments inserted therethrough for operating within the body cavity. Typically, an access assembly includes a housing configured for receiving an instrument, and a tubular member rigidly affixed to the housing and configured for insertion into a body cavity.

In order to provide a greater space in which a surgeon may operate and to increase visibility within the body cavity, the body cavity is generally insufflated. To avoid gas leakage from within the cavity, various seal members have been developed. As an instrument is inserted into the access assembly and through the seal member, a seal is created about the instrument. Depending on the type of seal member used, manipulation of the instrument inserted therethrough may compromise the integrity of the seal. This is especially true of any lateral movement of the instrument relative to the access assembly. Lateral manipulation of the instrument may cause the seal member to stretch non-uniformly, resulting in a phenomenon commonly referred to as "cat-eyeing." To prevent "cat-eyeing" of a seal member, and, thereby prevent leakage of gas through the access assembly, the lateral manipulation of an instrument inserted therethrough may be limited.

Therefore, it would be beneficial to have an access assembly including a housing configured to maintain a seal member mounted therein relative to an instrument inserted therethrough as the instrument is being manipulated.

SUMMARY

In accordance with one embodiment of the present disclosure, an access assembly includes a housing defining a longitudinal axis and having a longitudinal opening therethrough, a cannula extending distally from the housing and in fluid communication with the longitudinal opening and a seal member mounted within the longitudinal opening of the housing. The seal member is configured to receive an instrument therethrough in substantial sealed relation therewith. The housing is adapted to move in at least a radial direction with respect to the longitudinal axis whereby the seal member maintains the substantial sealed relation relative to the instrument as the instrument in manipulated. The housing may be flexible and capable of deflection relative to the longitudinal axis. The housing may comprise an elastomeric material in whole or in part. The seal member may be integrally formed with the housing. The housing may include at least one flexible ring portion and possibly a plurality of ring portions.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DETAILED DESCRIPTION

Figure 1:
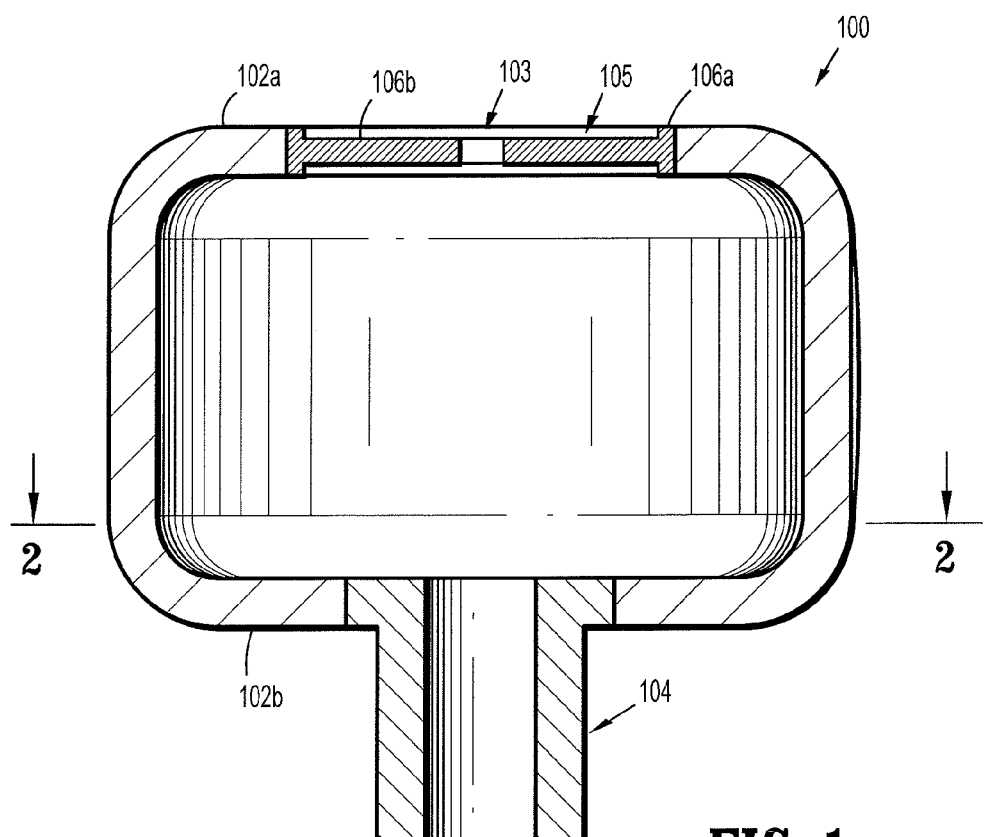
FIG. 1 is a cross-sectional side view of an access assembly according to aspects of the present disclosure.

Referring now to the drawings wherein like reference numerals illustrate similar components throughout the several views. As shown in the drawings and as described throughout the following description, as is traditional when referring to relative positioning on an object, the term "proximal" refers to the end of the apparatus which is closer to the user and the term "distal" refers to the end of the apparatus which is further from the user.

FIGS. 1-5 illustrate a trocar assembly 100 in accordance with the principles of the present disclosure. Referring initially to FIG. 1, trocar assembly 100 includes a housing 102 and a cannula 104 extending distally therefrom. Cannula 104 may be integrally formed with housing 102. Alternatively, cannula 104 may be securely attached to housing 102 using adhesive, mechanical fasteners or other suitable attachment means. It is further envisioned that cannula 104 may be selectively attachable to housing 102, e.g. a threaded connection. Trocar assembly 100 may be configured for use with any known endoscopic or laparoscopic instrument.

Cannula 104 may be constructed of metal, plastic or other suitable material. Cannula 104 may include a blade or piercing tip (not shown) for penetrating a body cavity. Alternatively, cannula 104 may be configured to receive an obturator (not shown) for assisting in penetration of a body cavity. Cannula 104 is preferably rigid, however, cannula 104 may also be flexible. Cannula 104 may include one or more seals (not shown) spaced along the length thereof. Cannula 104 may also be modified for engagement with other known access assemblies.

Figure 2:
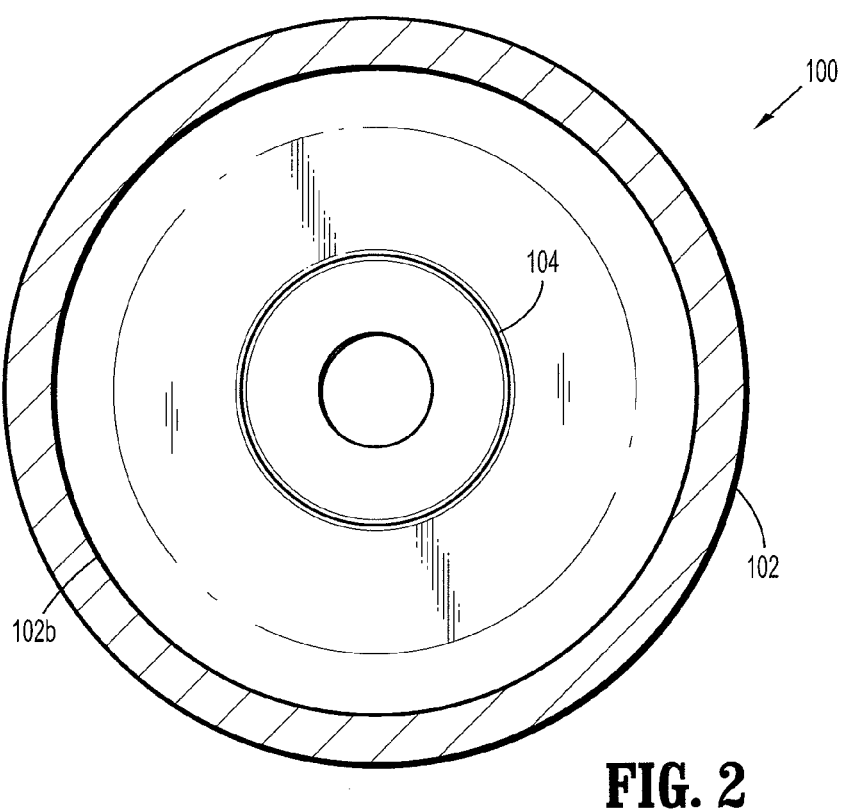
FIG. 2 is a cross-sectional top view of the access assembly of FIG. 1 taken along line 2-2.

Turning now to FIGS. 1 and 2, housing 102 forms a substantially annular member having a partially closed proximal end 102a and a partially closed distal end 102b. Housing 102 may instead define an oval, square, rectangular or other suitable profile. Housing 102 may be constructed of plastic, rubber, polymer, or other suitable flexible material. Proximal end 102a of housing 102 defines an opening 103 therein configured to maintain a seal member 105. Opening 103 and seal member 105 may be configured to receive instruments of various diameters and configurations. As will be discussed below, housing 102 is configured to move or flex at least in a radial direction relative to the longitudinal axis "x" of cannula 104 as an instrument "E" (FIG. 3), inserted through seal member 105, is manipulated. In this manner, seal member 105 may be maintained relative to instrument "E", thereby preventing "cat-eyeing" of seal member 105. Proximal end 102a of housing 102 may be configured with a tab(s) and/or a latch(es) (not shown) for selectively securing instrument "E" to housing 102, thereby more securely maintaining instrument "E" relative to housing 102 and thus, seal member 105. Housing 102 also may include a valve or port (not shown) configured for supplying insufflation gas to the body cavity.

Seal member 105 spans opening 103 and is configured to receive instrument "E" (FIG. 3) therethrough. Seal member 105 may include any number of seal configurations, including but not limited to a septum valve with an aperture, a flap valve, slit valve, and zero closure seals. As shown, seal member 105 includes an outer ring 106a and an inner seal surface 106b. Outer ring 106a of seal member 105 is configured for operable engagement within opening 103 formed in housing 102. Outer ring 106a may be affixed to housing 102 using adhesive, bonding or by any other suitable means. Alternatively, outer ring 106a may include a lip, groove, threading or other configuration (not shown) for selective engagement with a corresponding groove, lip, threading or other configuration (not shown) formed on housing 102. Seal surface 106b defines an opening 105 configured for receiving instrument "E". Seal surface 106b may be constructed of rubber, plastic, polymer or other suitable material. Seal surface 106b may be formed of one or more layers of material and may be integrally formed with outer ring 106a. Seal member 105 may include reinforcement (not shown) for ensuring instrument "E" is centrally maintained through seal surface 106b.

The operation of trocar assembly 100 will now be described with reference to FIGS. 3-5. Cannula 104 of trocar assembly 100 is initially inserted into a body cavity in a manner similar to known trocar assemblies. As discussed above, cannula 104 may be configured to pierce through tissue and into the body cavity of a patient. Alternatively, trocar assembly 100 may be configured to operate with an obturator (not shown). Once cannula 104 is received in the body cavity, the obturator, if used, may be removed, and trocar assembly 100 is ready to receive instrument "E" therethrough.

Figure 3:
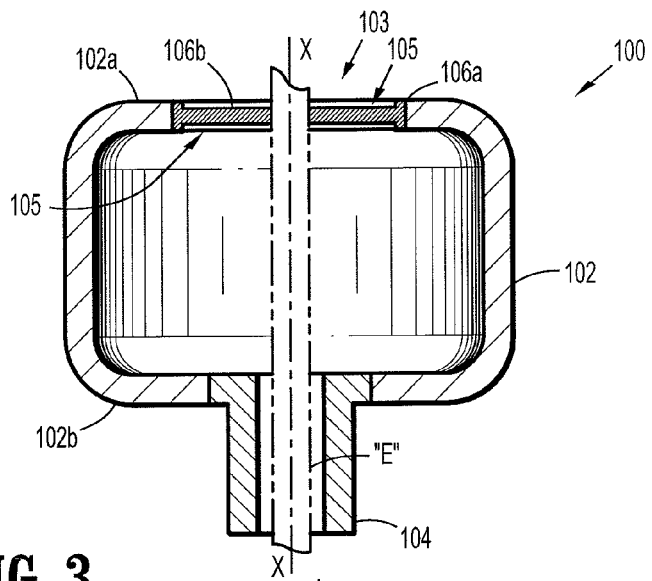
FIG. 3 is a cross-sectional side view of the access assembly of FIGS. 1 and 2 including an instrument inserted therethrough, in a first or initial position.

Referring initially to FIG. 3, in a first or relaxed position housing 102 and cannula 104 define a central axis x-x prior to and upon initial insertion of instrument "E" therethrough. In this first position, seal surface 106b of seal member 105 is securely received about instrument "E" and the longitudinal axis of instrument "E" is aligned with central axis x-x. In this manner, seal surface 106b of seal member 105 is uniformly stretched about instrument "E", thereby creating an airtight seal between housing 102 and with instrument "E".

Figure 4:
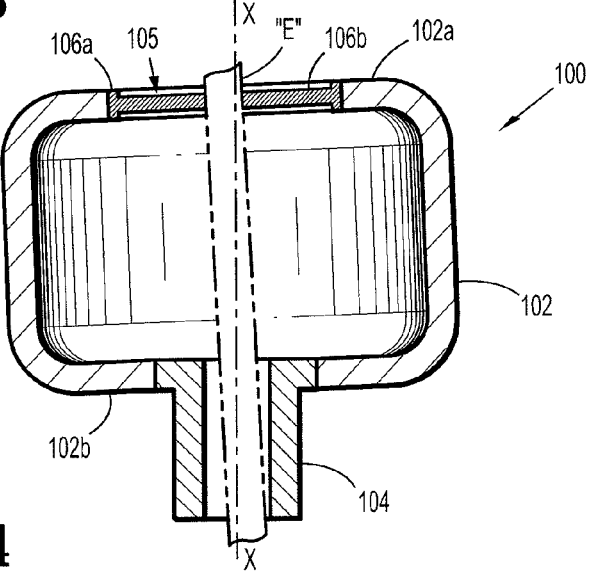
FIGS. 4-5 are cross-sectional side views of the access assembly of FIGS. 1-3, in flexed positions.
Figure 5:
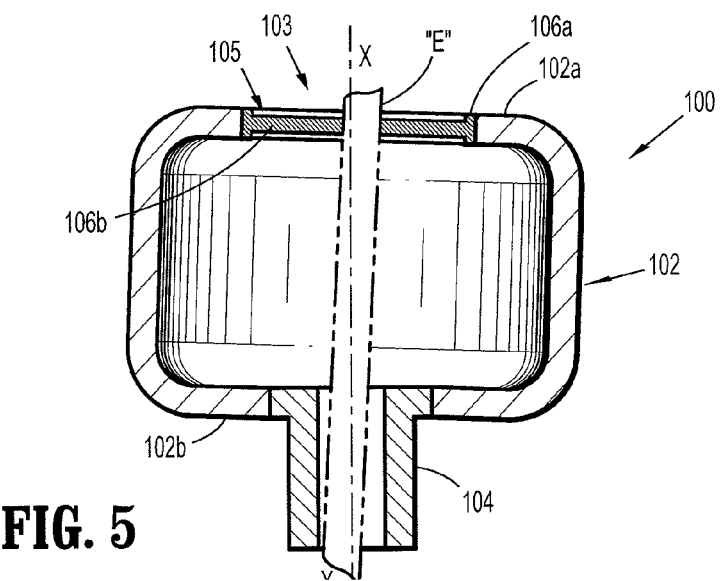
Figure 6:
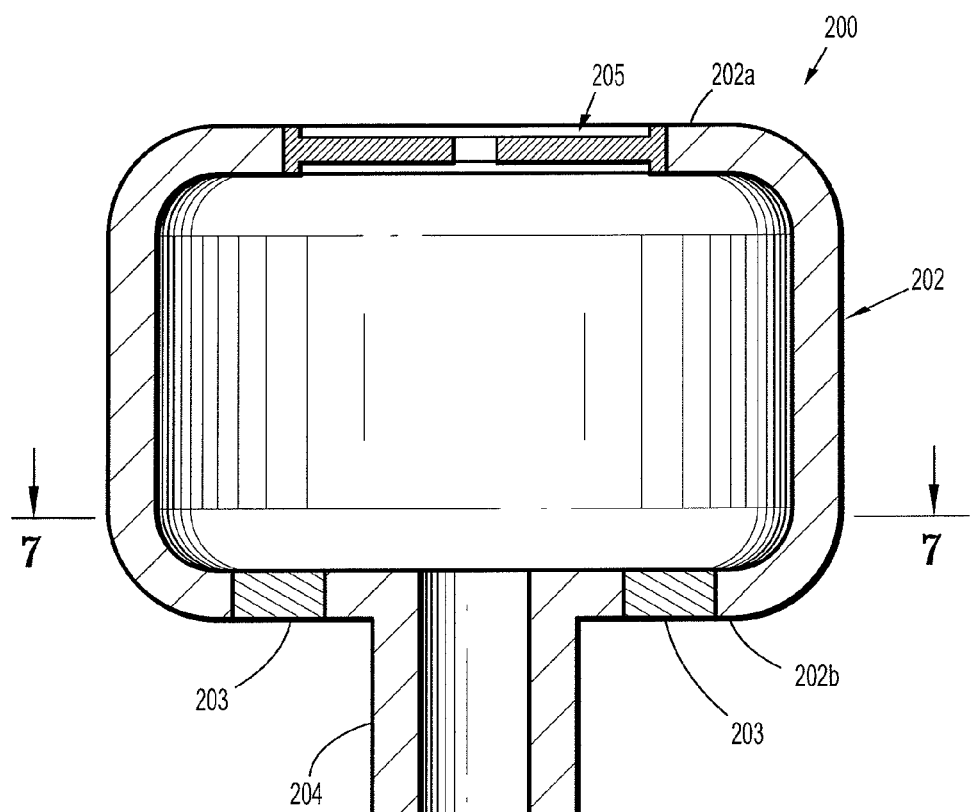
FIG. 6 is a cross-sectional side view of another access assembly according to aspects of the present disclosure.
Figure 7:
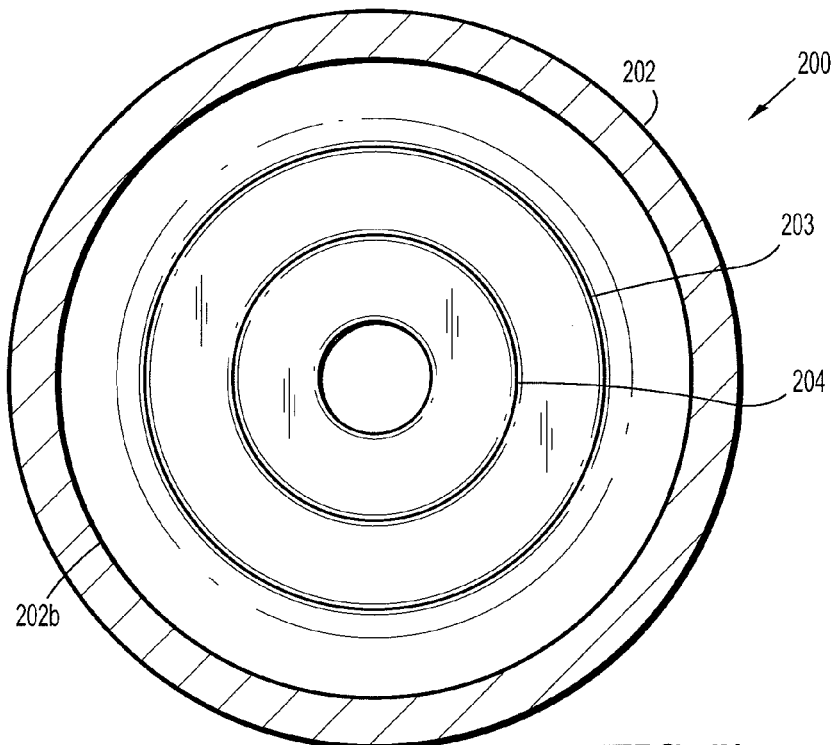
FIG. 7 is a cross-sectional top view of the access assembly of FIG. 6 taken along line 7-7.

Turning now to FIGS. 4 and 5, as instrument "E" is manipulated within trocar assembly 100 the longitudinal axis of instrument "E" moves out of alignment with central axis x-x defined by housing 102 and cannula 104. As a distal end of instrument "E" manipulated, housing 102 deforms or flexes to maintain seal member 105 relative to instrument "E". In this manner, seal surface 106b of seal member 105 is prevented from stretching, or "cat-eyeing, as instrument "E" is moved laterally in relation to longitudinal axis "x" of cannula 104. All or a portion of housing 102 may be configured to flex in response to manipulation of instrument "E".

Referring now to FIGS. 6-10, an alternate embodiment of an access assembly is shown generally as trocar assembly 200. Trocar assembly 200 is substantially similar to trocar assembly 100 described hereinabove, and will only be described as relates to the differences therebetween. Trocar assembly 200 includes a housing 202 and a cannula 204. As shown, cannula 204 is integrally formed with housing 202. Cannula 204 may instead be securely attached to housing 202 using adhesive, mechanical fasteners or other suitable attachment means. Alternatively, cannula 204 may be selectively attachable to housing 202, e.g. a threaded connection. Trocar assembly 200 may be configured for use with any known endoscopic or laparoscopic instrument.

Housing 202 defines a substantially annular housing including proximal and distal ends 202a, 202b. Proximal end 202a of housing 202 includes a seal member 205. Housing 202 further includes a flexible ring portion 203. Flexible ring portion 203 may be formed of rubber, plastic, polymer or other suitable flexible material. Flexible ring portion 203 is positioned on distal end 202b of housing 202 and extends about cannula 204. Flexible ring portion 203 may be integrally formed with housing 202. Flexible ring portion 203 may also be integrally formed with cannula 204, or both cannula 204 and housing 202. Flexible ring portion 203 may include a coating (not shown) for sealing flexible ring portion 203 with housing 202 and/or for strengthening flexible ring portion 203.

Figure 8:
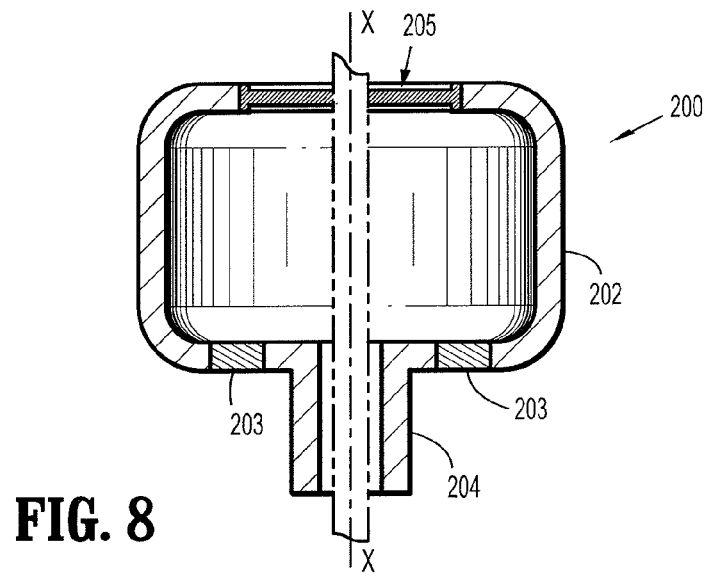
FIG. 8 is a cross-sectional side view of the access assembly of FIGS. 6 and 7 including an instrument inserted therethrough, in a first or initial position.
Figure 9:
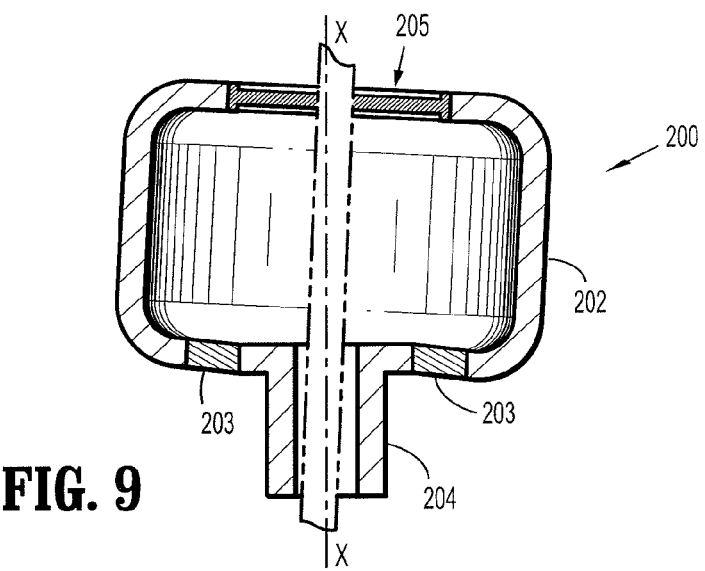
FIGS. 9 and 10 are cross-sectional side views of the access assembly of FIGS. 6-8, in flexed positions.
Figure 10:
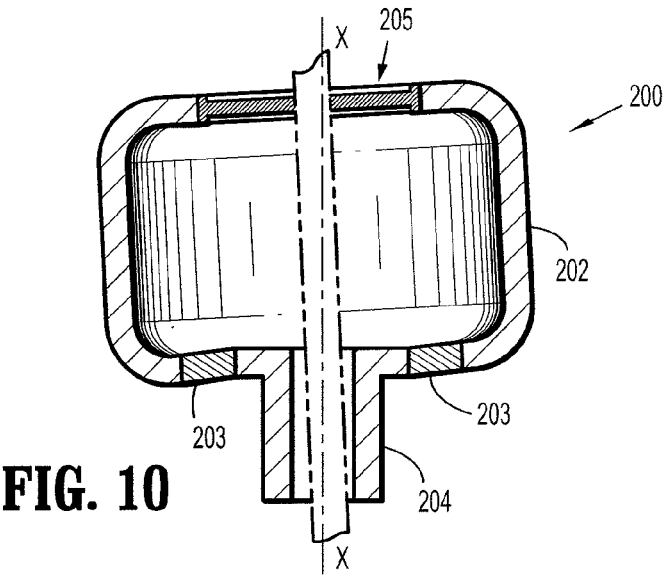

Access assembly 200 operates in much the same manner as access assembly 200. Referring now to FIGS. 8-10, an instrument "E" is inserted through seal member 205 of access assembly 202. Manipulation of instrument "E" exerts a force on seal member 205 which is maintained in housing 202. Flexible ring portion 203 permits housing 202 to move in response to the manipulation of instrument "E". In this manner, seal member 205 is moved relative to instrument "E" inserted therethrough, thereby preventing "cat-eyeing" of seal member 205 and leakage of insufflation gas therethrough.

Figure 11:
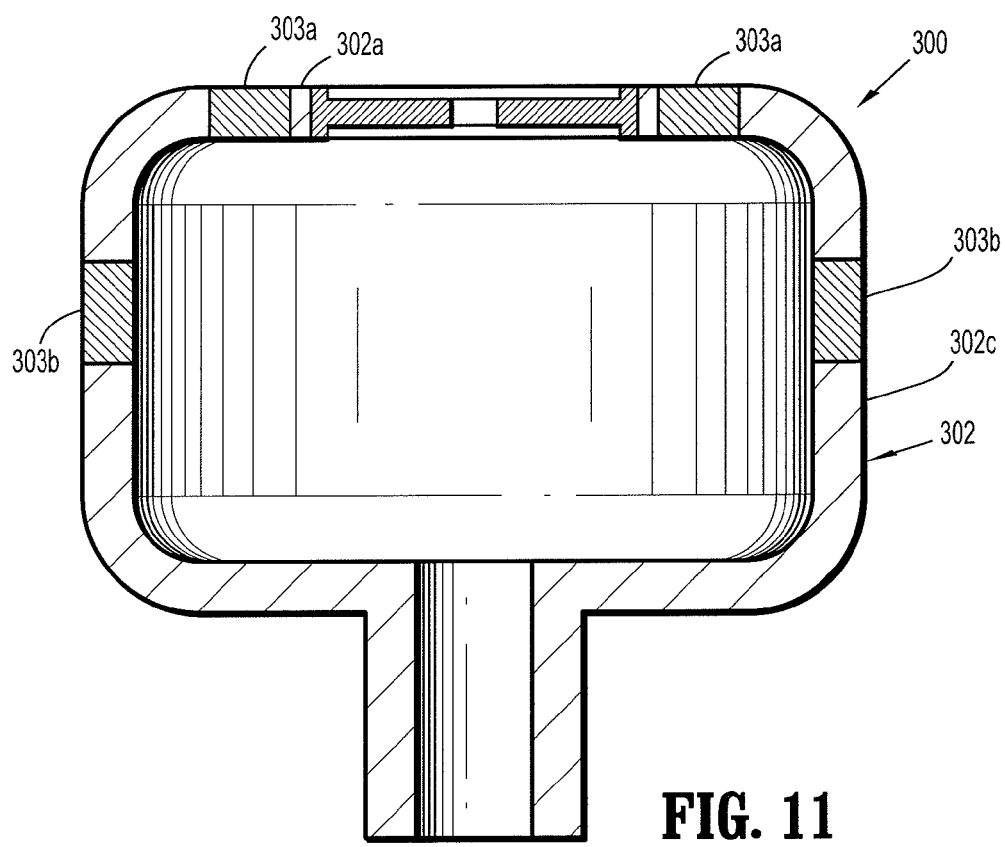
FIG. 11 is a cross-sectional side view of another access assembly according to the present disclosure.
Figure 12:
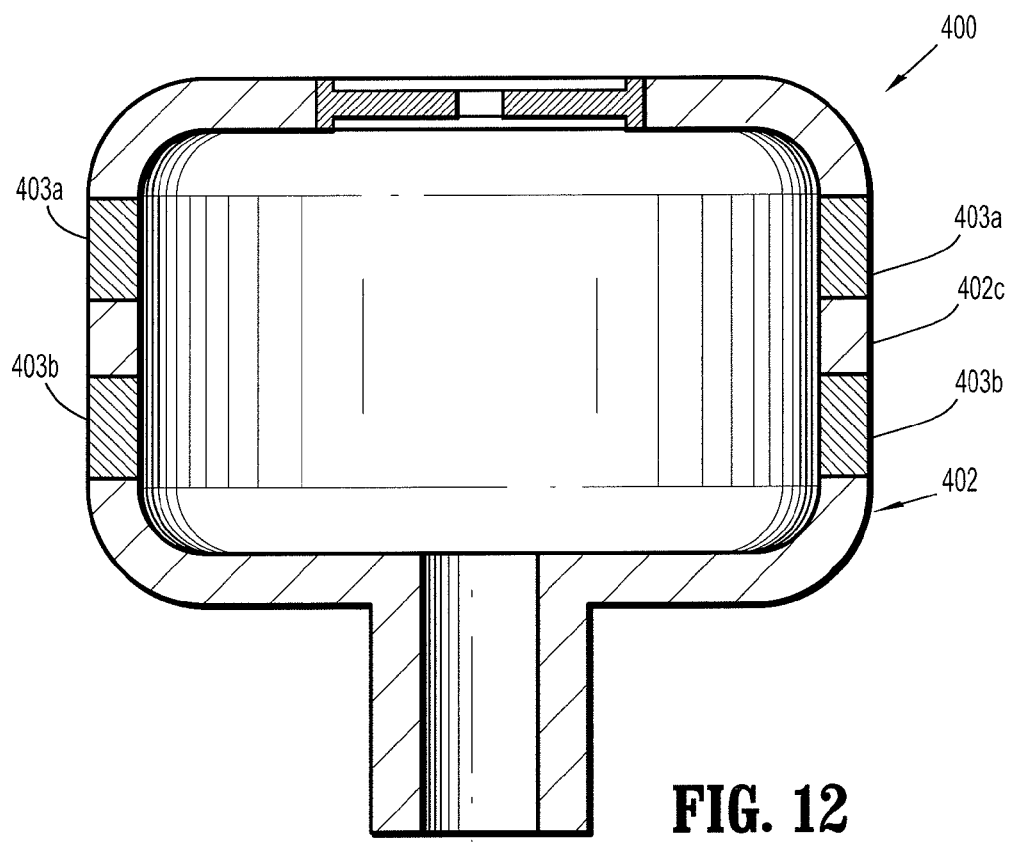
FIG. 12 is a cross-sectional side view of yet another access assembly according to the present disclosure.

Turning now to FIGS. 11 and 12, alternate embodiments of access assemblies according to the present disclosure are shown generally as access assemblies 300, 400. Access assemblies 300, 400 include multiple flexible ring portions 303a, 303b, 403a, 403b, respectively. Access assembly 300 includes a first flexible ring portion 303a positioned within proximal end 302a of housing 302 and a second flexible ring portion 303b positioned within sidewall 302c of housing 302. Access assembly 400 includes first and second flexible ring portions 403a, 403b positioned within sidewall 402c. Multiple flexible ring portions 303a, 303b, 403a, 403b permit greater flexibility of housing 302, 402, thereby permitting manipulation of instrument "E" through a greater range of motion.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. An access assembly comprising:
   a housing having a longitudinal opening therethrough, the housing having a proximal face and a distal face;

a cannula integrally formed with and extending from the housing, the cannula in fluid communication with the longitudinal opening and defining a longitudinal axis;

a seal member mounted to the housing, the seal member configured to receive an instrument therethrough in substantial sealed relation therewith; and a flexible annular segment mounted along the distal face of the housing in substantially coplanar relation therewith, the annular segment dimensioned and adapted to facilitate movement of the housing in at least a radial direction with respect to the longitudinal axis whereby the seal member maintains the substantial sealed relation relative to the instrument as the instrument is manipulated.

2. The access assembly of claim 1, wherein the housing is flexible.

3. The access assembly of claim 1, wherein the housing is formed of rubber.

4. The access assembly of claim 1, wherein the seal member is integrally formed with the housing.

5. The access assembly of claim 1, wherein the annular segment is dimensioned to define at least one flexible ring.

6. The access assembly of claim 1, wherein the annular segment is dimensioned to permit the distal face of the housing to articulate and/or pivot relative to the cannula.

7. The access assembly of claim 6, wherein the annular segment is directly connected to the cannula member.

8. The access assembly of claim 6, wherein the annular segment defines a general ring shape.

9. The access assembly of claim 6, wherein the seal member is mounted to the proximal face of the housing.

* * * * *